United States Patent [19]
Cohen et al.

[11] Patent Number: 5,275,563
[45] Date of Patent: Jan. 4, 1994

[54] DENTAL POST EXTRACTING DRILL

[75] Inventors: Brett I. Cohen, Nanuet; Barry L. Musikant; Allan S. Deutsch, both of New York, all of N.Y.

[73] Assignee: Essential Dental Systems, Inc., South Hackensack, N.J.

[21] Appl. No.: 939,126

[22] Filed: Sep. 2, 1992

[51] Int. Cl.⁵ .................... A61C 5/02; A61C 5/08
[52] U.S. Cl. ............................. 433/224; 433/220; 433/221
[58] Field of Search ............ 433/220, 221, 224, 225, 433/173, 174

[56] References Cited

U.S. PATENT DOCUMENTS

| | | |
|---|---|---|
| 693,884 | 2/1902 | Nagy. |
| 3,524,255 | 8/1970 | Kurer ..................... 32/13 |
| 3,919,774 | 11/1975 | Fishman .................. 32/15 |
| 4,234,309 | 11/1980 | Sellers ................... 433/225 |
| 4,239,489 | 12/1980 | Ellman et al. ........... 433/220 |
| 4,449,937 | 5/1984 | Weissman ............... 433/225 |
| 4,553,942 | 11/1985 | Sutter ................... 433/225 |
| 4,579,531 | 4/1986 | Hinks .................... 433/225 |
| 4,622,012 | 11/1986 | Smoler .................. 433/221 |
| 4,728,292 | 3/1988 | Lustig et al. ............ 433/225 |
| 4,729,736 | 3/1988 | Weissman ............... 433/221 |
| 4,746,292 | 5/1988 | Johnson ................. 433/224 X |
| 4,778,388 | 10/1988 | Yuda et al. .............. 433/221 |
| 4,846,685 | 7/1989 | Martin ................... 433/221 |
| 4,917,606 | 4/1990 | Miller ................... 433/225 |
| 5,035,620 | 7/1991 | Roane ................... 433/221 |
| 5,085,586 | 2/1992 | Johnson ................. 433/224 |
| 5,118,295 | 6/1992 | Stiles ................... 433/221 |
| 5,161,973 | 11/1992 | Johnson ................. 433/221 |

FOREIGN PATENT DOCUMENTS 2812175  9/1979  Fed. Rep. of Germany.
9101693  2/1991  World Int. Prop. O. .......... 433/225

Primary Examiner—Gene Mancene
Assistant Examiner—Nicholas D. Lucchesi
Attorney, Agent, or Firm—Gottlieb, Rackman & Reisman

[57] ABSTRACT

A method and apparatus for removing dental posts by inserting and rotating an extraction drill. It is particularly useful for hollow dental posts having left-handed helical grooves on the post's external surface.

4 Claims, 1 Drawing Sheet

DENTAL POST EXTRACTING DRILL

This invention relates to methods and apparatus for removing dental posts that have been implanted in the root canal of a tooth. The invention particularly relates to a right handed drill bit capable of lateral milling of the walls of the dental post or binding in the dental post and removing the post from the root canal. The invention is applicable in connection with a dental post that has been inserted into the root canal passively and relies on cement for attachment. It finds particular application with hollow dental posts having left handed helical grooves or a cross hatch pattern of grooves in their outside diameter enabling the cement to lock the post into position as it is inserted into the root canal.

BACKGROUND OF THE INVENTION

Dental posts are known having a head portion to allow the building of a tooth prosthesis thereon and are typically implanted in the root canal with the intent that they remain there for the life of the patient. Several types of posts are known to deal with the anomalies that are found in various teeth. One type, e.g. U.S. Pat. 3,919,774, employs an external screw thread to allow the post to cut a groove into the walls of the previously prepared open root canal. Others, e.g., U.S. Pat. 4,729,736, employ a helically grooved external surface which act as flute lines for escape of air and which, together with other structures, engage an adhesive inserted into the root canal thereby making the loosening of the dental post under the extreme stress of chewing less likely.

It has also been known to have to remove dental posts from a root canal. This has typically been necessary whenever an infection occurs along the previously cleaned root canal or where there has been post breakage, typically of the head portion. This presents a very difficult problem since the post is designed to remain and not to be removed. Typically the endodontist has to drill a bore having a diameter greater than that of the post thereby destroying the post. This is difficult because of the hardened materials (usually stainless steel or titanium) of which the post is made and may require grinding the post and greatly enlarging the root canal opening in the process. Such enlarging is done at the expense of the material forming the side wall of the tooth and results in the weakening of the tooth due to the future insertion of a dental post in the same root canal.

BRIEF DESCRIPTION OF THE INVENTION

This invention concerns a mechanical method and apparatus for enabling an endodontist to remove an implanted dental post in the root canal of a patient's tooth. The invention is particularly useful with dental posts having a smooth walled bore or channel along the length of the axis of the post. The dental post is removed by inserting an extracting drill into the opening of the bore and rotating the drill. The extracting drill has cutting surfaces at its tip, an axially extending right handed flute on its external surface and a head that is adapted to engage a dental hand piece for rotating the extracting drill clockwise from above. Because of the right handed flute and cutting surfaces, the extraction drill may enter the bore of the dental post and, with appropriately chosen dimensions, bind in the bore of the tooth after a few rotations. The binding may occur because either the cutting surface at the tip or the edges of the flute cut into the wall of the bore. Further rotation causes the dental post to loosen from its rigid implanted state by breaking the cement seal in the root canal and causes the dental post to begin to rotate in the same sense. Due to the normally left handed groove of the dental post, the post translates along its axis and leaves the root canal.

This invention has particular application with dental posts that have a hollow bore that allows the dentist to drill down through any soft material or adhesive present in the bore of the dental post. Such posts allow dental surgery using conventional reamers and files to reach the tip of the post (the apex) without removal of the post, but it may occur that the post has to be removed in any case. This invention provides a simple means for either drilling through the soft material, or if resistance is met, for removing the post.

It is an object of the present invention to provide a method for removing a dental post implanted in a root canal, said post having a bore with a predetermined diameter and length comprising the steps of inserting an extracting drill having a right handed helical flute along its outer surface into the opening of the bore in the dental post, said extracting drill having a head adapted to be received in a dental hand piece to rotate said extracting drill about its longitudinal axis; rotating said extracting drill clockwise from above to cause it to rigidly engage the walls of the bore; continuing to apply clockwise rotating torque to said extracting drill to cause said dental post to rotate about its axis within the root canal, wherein said dental post rotates and moves along its longitudinal axis to disengage from the root canal.

It is a further object of the present invention to provide an extracting drill having a head adapted to be received in a dental hand piece to cause said drill to rotate along a longitudinal axis thereof, said drill having a right handed helical flute in its outer surface.

DETAILED DESCRIPTION OF A PREFERRED EMBODIMENT

Figure 1:
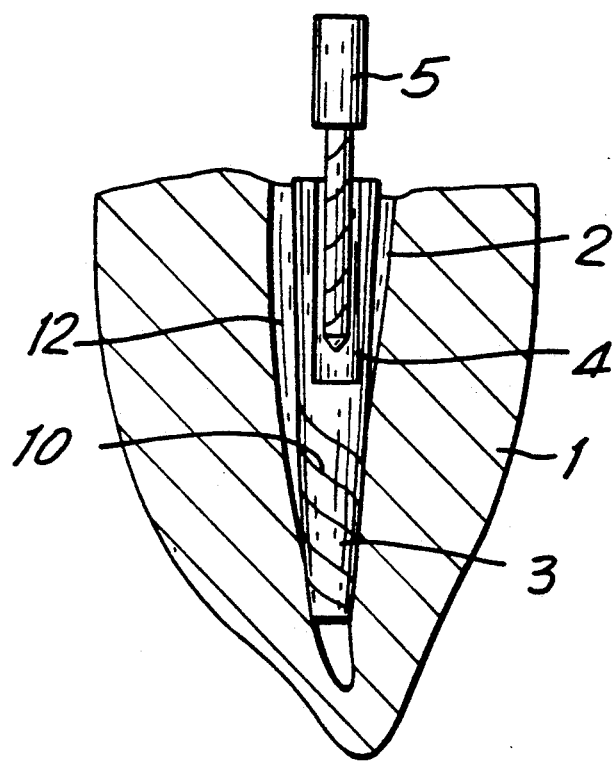
FIG. 1 is a cross-section view showing a dental post extracting drill located within a post that is in turn in the root canal of a tooth.

Referring to FIG. 1, a tooth 1 is shown having a root canal 2 therein into which has been placed a dental post 3. The dental post is preferably hollow. Hollow dental posts have the advantage that if an infection occurs at the distal end of the post, it would not be necessary to remove the post in order to treat the infection. The endodontist would have the option of clearing the bore in the post and introducing antibiotics directly therethrough and use conventional reamers and files to eliminate any debris.

The present invention, however, is concerned with removal of the dental post in the event that is necessary. For those cases in which the post is not hollow, a bore could be formed in the top of the post by drilling or grinding, and then the present invention utilized. The length of the bore should be as long as is convenient without endangering breaking the post 3.

Figures 2, 3:
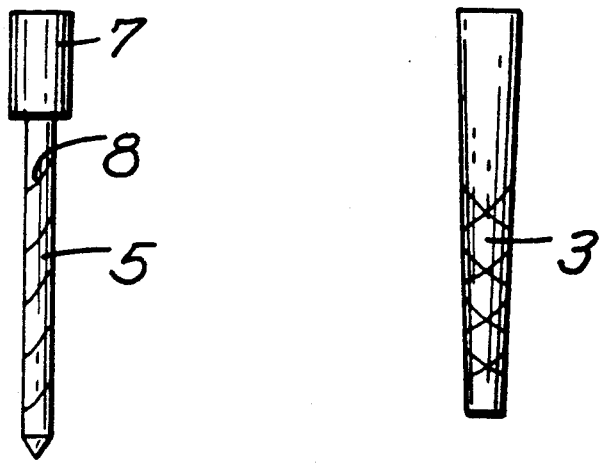
FIG. 2 is an enlargement of a cross-section of the extracting drill of the present invention.
FIG. 3 is a cross-section view of a dental post having cross-hatched grooves.

The bore then receives the extracting drill 5 shown in detail in FIG. 2. The extracting drill is a generally cylindrical drill having a head region 7 which is adapted to be received by a dental hand piece or turning chuck (not depicted) to enable rotating the drill about its long axis in a clockwise direction as seen from above. In this context, above means from the head end of the drill. The extracting drill 5 need be inserted into the bore 4 only so far as is necessary to bind in the bore. The drill has a right-handed helical flute and a right hand cutting tip; it is capable of sidewise reaming in which the sharp edges of the flute remove metal. The clockwise motion causes the extracting drill to advance downward with respect to FIG. 1 into the bore. Since clockwise motion from above normally extracts a left hand screw, the left hand grooves on the post 3 will, in general, prevent the post from freely turning in the clockwise from above direction. When the extracting drill binds in the post, further rotation will cause rotation of the left handed grooves 10 on the dental post to apply a force on the post causing it to move vertically upwards and be extracted from the root.

Alternatively, the post may be made with self-tapping threads that cut grooves into the walls of the root canal when the post is inserted. In order to release stresses that could split the tooth outwardly, it is known to divide the lower portion of the post to allow it to have flexibility to deflect inwardly and relieve the build up of stresses. In that case, the bore 4 should not be cut into the post deeper than the top of the split region. Also as shown in FIG. 3, a solid passive post lacking threads and having a cross hatch pattern of grooves relying on cement for attachment may also be used.

It is not required that helical grooves be provided in the walls of the root canal. In those circumstances where a threaded post is inserted directly into the bore of the root canal and adhered in place by use of an adhesive sealing the gap 12 between the root canal and the walls of the post 3, the invention is still a practical means of removing the post. This occurs because in effect, the adhesive forms channels around the threads of the post, which may be broken free from the adhesive by the torques developed by the hand piece. Rotation will cause the advance of the dental post in the same manner as if the walls of the root canal had been helically grooved.

The dimensions of the extracting drill are preferably 0.4, 0.7, 0.9, 1.1, 1.4 and 1.61 mm (outside diameter). They are for use with dental posts having an outside shaft diameter of 0.8, 1.1, 1.35 and 1.6 mm, for use in root canals opened to a diameter of 0.9, 1.2, 1.45 and 1.7 mm. The preferred combinations of post outside diameter and drill size is as follows For a post with outside diameter of 0.8 mm use drills with outside diameter of 0.4 or 0.7 mm. For a post with outside diameter of 1.1 mm, use drills with outside diameter of 0.7, 0.9, or 1.1 mm. For a post with outside diameter of 1.35 mm use drills with outside diameter of 0.9, 1.1, or 1.4 mm. For a post with outside diameter of 1.6 mm use posts with outside diameter of 1.1, 1.4, or 1.61 mm. These combinations of drill sizes with post diameters allows the endodontist four options: to drill away the entire post by using a drill of diameter greater than the post; to applying lateral pressure to a drill of smaller diameter so that the post is reamed to remove the entire post; to use the smaller diameter drill size within the bore of the post to retract the post from the root canal, to re-treat the root canal directly through the post which remains intact.

In use, one simply exposes the bore in the top of the dental post and inserts the tip of the extracting drill therein. A dental hand piece is then attached to the head of the extracting drill, which is then rotated in a clockwise direction causing the extraction of the post.

The preferred embodiment has been described with orientations in one hand sense: namely, the right hand sense for the drill and the left hand sense for the grooves in the post. With these sense assignments, the drill is rotated with a clockwise orientation from above. An alternative embodiment may be achieved by reversing each sense (left hand sense for the drill and right hand sense for the grooves in the post) and reversing the orientation of the drill rotation (counterclockwise from above). It should be understood that the terms left and right are used in this generic sense so that the alternative embodiment may be deemed an equivalent representation.

Although the invention has been described in terms of a preferred embodiment, it should be understood that the invention is not limited to inessential details of the preferred embodiment and that the invention is determined by the scope of the following claims:

What is claimed is:

1. A method for removing a dental post implanted in a root canal and having a bore with a predetermined diameter and length and having a longitudinal axis parallel to the axis of the dental post comprising the steps of
   (a) inserting an extracting drill having a right handed helical flute along its outer surface into the opening of the bore in the dental post, said extracting drill having a head adapted to be received in a dental hand piece to rotate said extracting drill along its longitudinal axis,
   (b) rotating said extracting drill clockwise from above to cause it to rigidly engage the walls of the bore,
   (c) continuing to apply clockwise rotating torque to said extracting drill to cause said dental post to rotate about its axis within the root canal, wherein said dental post rotates and moves along its longitudinal axis to disengage from the root canal.

2. The method of claim 1 wherein said bore is formed in an initially solid dental post the bore formed with a pre-determined diameter and length and having its longitudinal axis parallel to the axis of the dental post.

3. A system for providing a support for a dental prosthesis and for removing said support comprising
   a dental post having a longitudinal bore of predetermined diameter therethrough and comprising a left-handed helical groove on the outer surface thereof and
   an extracting drill comprising means for engaging said bore in said post and having a head adapted to be received in a dental hand piece and rotated along a longitudinal axis thereof,
   said drill having a right-handed helical flute in its outer surface and having an outside diameter less than the diameter of said bore.

4. The system of claim 3 wherein said extracting drill is selected from a set having diameters greater than and less than the diameter of the bore, wherein the system may be used to drill away the post, remove the post by reaming, and retract the post to permit further medication to be applied to the tooth root.

* * * * *